United States Patent [19]

Bott

[11] Patent Number: 5,194,589
[45] Date of Patent: Mar. 16, 1993

[54] LEECH PROTEIN HAVING ANTICOAGULANT AND ANTIMETASTATIC PROPERTIES

[75] Inventor: John A. Bott, Grosse Pointe Shores, Mich.

[73] Assignee: Pennsylvania Hospital, Philadelphia, Pa.

[21] Appl. No.: 657,356

[22] Filed: Feb. 15, 1991

Related U.S. Application Data

[63] Continuation of Ser. No. 144,453, Jan. 5, 1988, abandoned, which is a continuation-in-part of Ser. No. 88,432, Aug. 26, 1987, abandoned, which is a continuation-in-part of Ser. No. 908,581, Sep. 18, 1986, abandoned.

[51] Int. Cl.$^5$ .................. C07K 13/00; C07K 3/02; C07K 3/28
[52] U.S. Cl. .................... 530/350; 530/413; 530/416; 530/855
[58] Field of Search .............. 530/350, 413, 416, 858, 530/855; 514/21, 12

[56] References Cited

U.S. PATENT DOCUMENTS 3,432,596 3/1969 Markwardt et al. ........... 530/858 X
4,588,587 5/1986 Gasic ..................... 424/95

OTHER PUBLICATIONS

Iwakawa et al. (1986) Clin. Expl. Metastasis 4(3):205-220.
Gasic et al. (1984) Problems and Proceedings, London, 275-278.
Gasic et al. (1984) Cancer Res. 44:5670-5676.
Murer et al. (1984) Thrombosis & Haemostasis 51(1):24-26.
Gasic et al. (1984) Proceedings of AACR 25: p. 58, abstract 229.
Bajkowski et al. (1984) Proceedings of AACR 25: p. 58, abstract 230.
Haementeria Officialis, International Conference, Jul. 1986, abstract.
Gasic et al. (1983) Cancer Res. 43:1633-1636.
G. J. Gasic et al., "Treatment of Experimental Metastasis by a Purified Protein from Leech Salivary Glands," in Treatment of Metastasis, Abstracts, 1st Meeting of Metastasis Research Society, Apr. 3-4, 1986, p. 25.
G. J. Gasic, et al., "Isolation of Protein from Salivary Glands of the Leech Haementeria Officinalis with Potent Antimetastatic and Anticoagulant Activity", in Proceedings of AACR, vol. 27, No. 261, Mar. 1986.
G. J. Gasic, "Leeches in Cancer Research: Isolation of a Purified Protein From Salivary Gland Extracts (SGE) of *Haementeria Officinalis* with Potent Antimetastatic and Anticoagulant Activities", British Association of Leech Scientists, International Conference, Jul. 11-12, 1986.
Scott et al, "Protease Nexin Properties and a Purification Procedure," Journal of Biological Chemistry, vol. 260, No. 11, pp. 7029-7034, Jun. 10, 1989.
Scott et al., "Purification of Human Protease Nexin," in The Journal of Biological Chemistry, vol. 258, No. 17, pp. 10439-10444, Sep. 10, 1983.
D. L. Eaton et al., "Prufication of Human Fibroblast Urokinase Proenzyme and Analysis of Its Regulation by Proteases and Protease Nexin," in The Journal of Biological Chemistry, vol. 259, No. 10, pp. 6241-6247, May 25, 1984.

Primary Examiner—Robert A. Wax
Assistant Examiner—Richard C. Ekstrom
Attorney, Agent, or Firm—Ratner & Prestia

[57] ABSTRACT

The present invention comprises a biochemically pure protein, termed antistasin, which exhibits both antimetastatic and anticoagulant properties. Methods of producing the protein and methods of using the protein to inhibit or reduce metastasis and/or coagulation of blood are disclosed. The complete amino acid sequences of antistasin and some variants have been determined from purified protein and cloned cDNAs.

14 Claims, 3 Drawing Sheets

FIG. 3

LEECH PROTEIN HAVING ANTICOAGULANT AND ANTIMETASTATIC PROPERTIES

This application is a continuation of application Ser. No. 07/144,453, filed Jan. 15, 1988, now abandoned which is a Continuation-in-Part of U.S. application Ser. No. 088,432, filed Aug. 26, 1987, now abandoned which is a Continuation-in-Part of U.S. application Ser. No. 908,581, filed Sep. 18, 1986, of common assignment herewith.

The present invention comprises a biochemically pure protein, termed antistasin, which exhibits both antimetastatic and anticoagulant properties. Methods of producing the protein and methods of using the protein to inhibit or reduce metastasis and/or coagulation of blood are disclosed.

FIELD OF THE INVENTION

The present invention pertains to a method of preparing and using a biochemically pure protein or proteins, each having anticoagulant and antimetastatic properties, and to the protein(s) itself. The complete amino acid sequence has been determined, including some variations thereof. The corresponding nucleotide sequence has been cloned and expressed.

BACKGROUND OF THE INVENTION

As disclosed in U.S. Pat. No. 4,588,587, of common assignment herewith, the saliva of blood sucking animals such as leeches, possesses anticoagulant activity. As also discussed in the above-referenced patent, an extract of certain leech salivary glands also exhibits antimetastatic effects. It has been postulated that these effects may result from a unique and complex combination of anticoagulants, and/or protease inhibitors, and/or other constituents of the extract which act synergistically.

The theoretical mechanism by which metastasis occurs is believed to involve several steps, such as entry of tumor cells into the organisms circulation (intravasculation); their transport by the blood stream; interactions of circulating malignant cells with platelets and plasma clotting factors with activation of the hemostatic system; interaction of the same cells with host cells other than platelets; arrest of tumor cells, surrounded by platelet aggregates and fibrin clots within capillaries; proteolytic attack of the blood vessel wall, particularly of its basement membrane, by tumor enzymes; escape from the circulation system (extravasculation); and formation of secondary tumors or colonies.

Crucial to this mechanism is the ability of the circulating tumor cell to initiate the formation of a blood clot which serves to lock the cell in a capillary. Falanga, et al (*Biochemistry* 24:5558–5567, 1985) isolated and characterized a particular cancer procoagulant which was shown to initiate coagulation through activation of factor X. In addition, other researchers cited in that reference have isolated cancer procoagulants which directly activate factor X. Finally, one of the present inventors' prior publications (Cancer Metastasis Reviews 3, 99–116 (1984) presents a summary of research into the activation of the coagulation system by tumor cells, which also discusses the possible involvement of factor X.

BRIEF DESCRIPTION OF THE INVENTION

The present invention comprises a newly isolated, biochemically pure protein (or proteins) having antimetastatic and anticoagulant properties. This protein is derived from a leech salivary gland, specifically that of the Mexican leech, *Haementeria officinalis*. The invention also comprises a method of isolating the protein, and a method of using the protein to prevent or delay blood coagulation and metastasis. The protein, termed antistasin, is believed to inhibit coagulation of blood by inhibiting coagulation factor Xa but not thrombin.

Antistasin of this invention is also useful in the prevention, prophylaxis, therapy and treatment of thrombotic diseases.

The complete amino acid sequence has been determined, including some variations thereof. The corresponding nucleotide sequence has been cloned and expressed.

Antistasin is isolated from an extract of salivary glands of leeches, particularly the Mexican leech *Haementeria officinalis*, by heparin affinity chromatography followed by anion exchange chromatography. The isolated antistasin has a molecular weight of approximately 17,000 under nondenaturing conditions. The protein has an isoelectric point of approximately 9.5 and is extremely active as an inhibitor of coagulation in in vitro analysis. Furthermore, the extract has been shown to be useful in inhibiting metastasis in in vivo tests using mice.

DETAILED DESCRIPTION OF INVENTION

Antistasin is a biochemically pure protein or proteins, each of which is separated from a leech salivary gland extract by chromatography and selection of chromatographic fraction having anticoagulation activity. The product antistasin(s) are characterized by a selective capacity to inactivate factor Xa, but not thrombin.

Antistasin is purified to two different stages, Stage 1 having partial purity, and Stage 2 having apparent homogeneity.

Preliminary data on sequencing proteolytic digests of the apparently homogeneous preparation (Stage 2) suggest the possibility of natural homologues, isoforms or genetic variants of antistasin. This invention encompasses all such homologues, isoforms or genetic variants, provided that each one has inhibitory activity against Factor Xa.

It will be understood that other variants of any of the antistasins of the present invention are included, especially any variants that differ from the isolated antistasins only by conservative amino acid substitution All such conservative amino acid substitutions are defined as "sets" in Table 1 of Taylor, W. R., J. Mol. Biol. 188, 233 (1986). Antistasin or fragments thereof in this application includes any such variations in the amino acid sequence, whether by conservative amino acid substitution, deletion, or other process, provided that the antistasin, after purification, immunochemically reacts with antibodies specific for antistasin isolated from the Mexican leech, *Haementeria officinalis*, and inhibits Factor Xa.

Oligonucleotide probes were constructed from the amino acid sequence of the isolated, purified antistasin protein. These probes were then employed to screen for the cDNA clones encoding antistasin. Clones containing antistasin cDNA(s) were used to transcribe antistasin mRNA, which was then translated and expressed in vitro. Work on expression of antistasin protein in a recombinant expression system is currently in progress.

Following is an example of this separation and selection method through the first stage of purification.

Method of Making Antistasin

Stage 1

An extract of the salivary gland of the Mexican leech is first prepared by extracting the dissected anterior and posterior salivary glands at 4° C. by sonication in a buffer of 20 mM HEPES (4-(2-hydroxyethyl)-1-piperazine ethane sulfonic acid), pH 7.8 containing 10 mM $CaCl_2$. The sonicated material is centrifuged at 8500 g for 20 minutes and the supernatants pooled and centrifuged at 100,000 g for 1 hour. The resulting supernatant protein suspension is frozen at −70° until needed. The antistasin is purified from the salivary gland extract by a two step chromatographic procedure using prolongation of the prothrombin time as an indicator of the presence of anticoagulant/antimetastatic activity.

The salivary gland extract is first placed on a heparin-agarose column equilibrated with 20 mM Tris-HCl, pH 8.7. Loading, washing, and elution of the heparin-agarose column are facilitated by the use of a gradient maker and liquid chromatography controller. Protein peaks eluting from the column are monitored by means of a UV monitoring system. The proteins not adhering to the column, and those which elute on wash with Tris buffer until no more adsorbance at 280 nM is observable are discarded. The washed column is then eluted by a combination of linear and step gradients using Tris buffer and Tris buffer containing 1M NaCl. When protein peaks begin eluting, the gradient is held manually and proteins are allowed to elute from the column under isocratic conditions. After each protein peak elutes, the gradient is restarted.

The column fractions containing anticoagulant activity, as determined by assay for anticoagulation activity, are thereafter pooled, concentrated by centrifugation through ultrafiltration filters having molecular weight exclusion limits of 12,000, desalted on small columns of G-25 Sephadex and applied to a mono Q column equilibrated in Tris buffer. The mono Q column is then washed and eluted in a manner similar to that of the heparin-agarose column, yielding antistasin (Stage 1).

Figure 1:
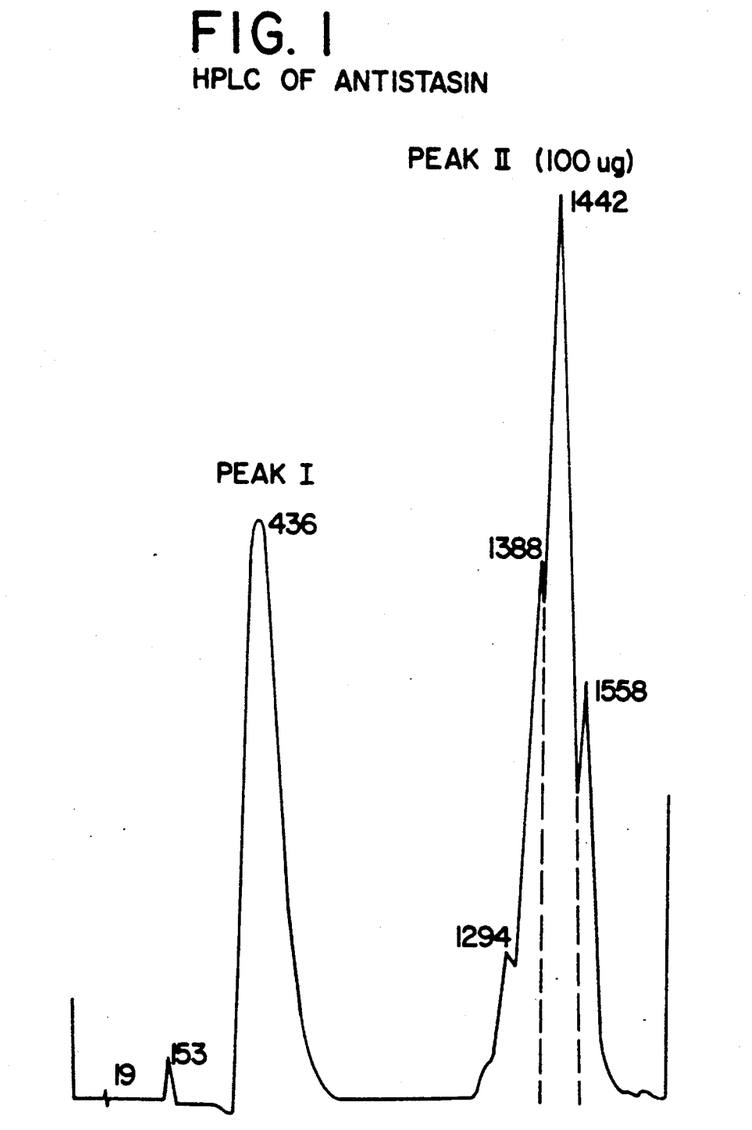
FIGS. 1, 2 and 3 are each curves showing the absorption spectrum, at 210 nm, of fractions eluted from a high pressure liquid chromatographic column, as further described in the detailed description. Numbers adjacent the peaks in the Figures indicate retention time in $10^{-2}$ minutes.

The partially purified protein derived in this manner is concentrated to 1 mg/ml and stored frozen at −70 degrees in Tris buffer. Further purification and analysis to Stage 2 grade purity is described in the Example, FIGS. 1-3 and Table 5.

Characteristics Of Antistasin

The molecular weight of the antistasin has been estimated by gel filtration on a fast protein liquid chromatograph and by SDS-gel electrophoresis. These analyses indicate a molecular weight of about 17,000.

The isoelectric point of the antistasin was measured by chromatofocusing on a mono P column using the fast protein liquid chromatograph. This method yielded a pI of 9.5 for the material.

Amino acid analysis of the partially purified antistasin (Stage 1) was conducted on a Glenco MM-70 amino acid analyzer. The antistasin material was hydrolyzed with 6 NHCl for 24 hours. The resulting amino acid composition is presented as Table 1. Slightly different results are obtained with greater apparent protein purity, see Table 5. Another analysis of the Stage 1 purified product, indicated a somewhat different amino acid content, as shown in Table 1A. This may indicate the possible presence of somewhat different forms of antistasin in the Stage 1 product, or contaminants or derivatives thereof.

Measurement Of Antimetastatic Properties

Inhibition of experimentally induced metastasis was determined by injecting antistasin or a buffer control two hours prior to injection of $10^5$ T241 tumor cells followed by innoculation of similar quantities of antistasin two and four hours respectively after injection of the tumor cells.

After 14-19 days, the animals were sacrificed and the lung tumor colonies counted. Results are presented as Table 2.

Anticoagulant Effects

One-stage clotting assays for measurement of the effect of antistasin on the prothrombin time, activated partial thromboplastin time, thrombin time, and factor X assay were performed at 37° C. in a final volume of 0.3 ml with the aid of a fibrometer. For the determination of the effect of antistasin on the prothrombin time, 100 ul of a saline dilution of protein followed by 100 ul of thromboplastin reagent containing 0.025M $CaCl_2$ was added sequentially to 100 ul of normal human plasma and the clotting time determined.

For measurement of activated partial thromboplastin time, kaolin-cephalin reagent containing 0.025M $CaCl_2$ was substituted for the thromboplastin reagent.

For measurement of the effect of antistasin on the thrombin time, the substrate solution was either 100 ul of normal human plasma or a 100 ul solution of a 1 mg/ml of fibrinogen in HEPES buffered saline and was clotted by the addition of 200 ul of a 0.30 unit/ml HEPES buffered saline solution of thrombin containing various amounts of purified antistasin. To maximize the effect on thrombin, 10 ul volumes of protein and thrombin were first incubated together for 5 minutes at 37 degrees before dilution and addition to the normal human plasma or fibrinogen.

For determination of the effect of antistasin on factor Xa activity, 100 ul of factor X deficient plasma was treated with 100 ul of 0.025M $CaCl_2$ followed by 100 ul of purified factor Xa or 100 ul of purified factor Xa containing various amounts of antistasin.

The results of the above-described assays are presented in Tables 3 an 4.

The analyses conducted indicate that antistasin is a protein having a molecular weight of approximately 17,000 in a single chain with an isoelectric point of 9.5. Antistasin is a potent anticoagulant of both human and mouse plasma As demonstrated in the various clotting time assays, antistasin acts through inhibition of the factor Xa pathway, rather than through interference with thrombin. Interestingly, the anticoagulant activity of antistasin appears more pronounced in vitro than in vivo. However, possible interferences have not been fully examined at this time.

Statement Of Industrial Utility

The protein or proteins of the present invention are useful for the treatment of mammals to prevent or reduce coagulation of blood or metastasis. Particular applicability encompasses prophylactic treatment for thrombosis related diseases.

EXAMPLE

A. Purification to Stage 2

Figure 2:
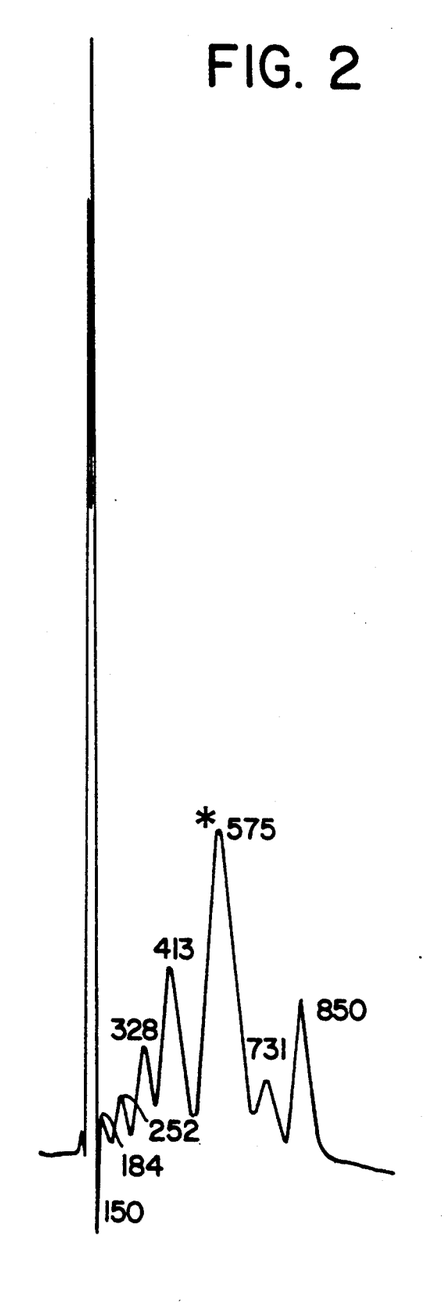
Figure 3:
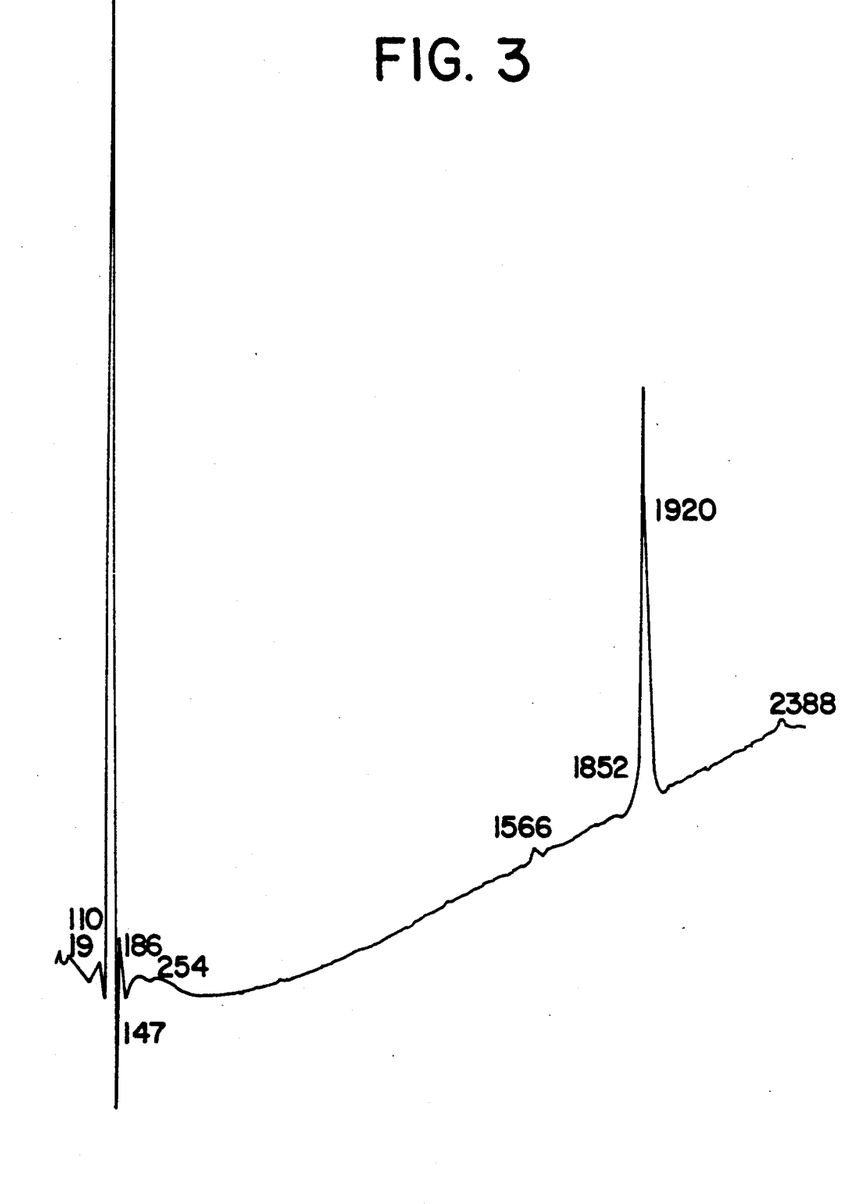

Antistasin was partially purified according to the method of Tuszynski, G.P. et al., J. Biol. Chem. 262, 9718-9723 (1987). The partially purified material was further purified utilizing reverse phase HPLC on an acetonitrile/water gradient (see FIG. 1). Factor Xa inhibitory activity appears in peak II, exclusively. Peak II contained a number of protein species and was further purified by reverse-phase HPLC utilizing an isopropanol/water gradient as shown in FIG. 2. The fifth peak (denoted with an asterisk [*]) contained the highest Factor Xa inhibitory activity. This material was purified to apparent homogenity as shown in FIG. 3, by HPLC utilizing an acetonitrile/water gradient, yielding antistasin (Stage 2).

B. Structural Analysis

The amino acid composition of antistasin (Stage 2) is shown in Table 5 (Glutamine (GLN) and Asparagine (ASN) are shown as Glutamic Acid (GLU) and Aspartic Acid (ASP) respectively due to the method of analysis used). The antistasin material was hydrolyzed with 6N HCL for 24 hours and analyzed on a Beckman Amino Acid Analyzer.

Antistasin (Stage 2) and fragments thereof were subjected to amino acid sequence analysis in an Applied Biosystems Gas Phase Sequencer, where amino acid residues are identified by an on-line HPLC detection system. The intact protein was blocked at its amino terminus rendering it resistant to sequence analysis. Accordingly, it was reduced and carboxy-methylated to modify cysteine residues and finally cleaved with the proteolytic enzyme, V8 protease, which cleaves at glutamic acid residues. Approximately 10 peptide fragments of antistasin (Stage 2) were produced by this cleavage reaction and purified by reverse phase HPLC utilizing an acetonitrile/water gradient. The amino acid sequence of one of these fragments is:
    PHE-CYS-LYS-CYS-ARG-LEU-GLU-PRO-MET-LYS-ALA-THR-CYS-ASP-ILE-SER-GLU-CYS-PRO-GLU.
Little contamination with other sequences was found for this particular fragment.

To determine the entire amino acid sequence, cleavages of intact antistasin (stage 2) were performed with V8 protease, supra, with cyanogen bromide (CNBr), which cleaves after methionine residues, and with chymotrypsin, which cleaves after phenylalanine and tyrosine residues. CNBr and chymotryptic fragments of antistasin were purified by HPLC and subjected to amino acid sequence analysis. Finally, the blocked amino terminus of antistasin, which rendered it resistant to N-terminal sequence analysis, was removed with the enzyme pyroglutaminase. This permitted an N-terminal sequence analysis to be performed on intact antistasin with its amino terminal residue enzymatically removed. The accumulated amino acid sequence analyses of pyroglutaminase-treated antistasin, as well as that of peptides generated by V8 protease, CNBr, and chymotrypsin cleavages is shown in Table 6.

Antistasin (stage 2) is a 119 amino acid polypeptide beginning with a blocked glutamine residue at its amino terminus and ending with a serine at its carboxyterminus. Antistasin (stage 2) contains 20 cysteine residues indicating the likely presence of 10 disulfide bridges. Heterogeneity in the amino acid sequence was observed at four positions in Antistasin (stage 2). At position 5 both an arginine and a glycine were observed in independent sequence analyses, while at position 35 both a methionine and valine residue were observed in independent analyses. Heterogeneity was also observed at positions 30 and 54 by nucleotide sequencing. This indicates that natural variants of antistasin exist and this invention encompasses all such variants, including natural and synthetic homologues, isoforms and genetic variants.

C. Complementary DNA Cloning, Sequencing and Expression

Total leech salivary gland RNA was obtained from dissected salivary glands of Haementeria officinalis by the method of Han, J. et al. Biochemistry 26, 1617 (1987). Poly A+ RNA was isolated according to Maniatis, T. et al. Molecular Cloning: A Laboratory Manual, Cold Spring Harbor Laboratory, Cold Spring Harbor, N.Y. 1982.

On the basis of amino acid sequence information, double-stranded oligonucleotides (110 base pairs) were designed according to the method of Ullrich, A. et al. EMBO J. 3, 361 (1984) with the codon usage frequency of Drosophila. To label, two complementary single-stranded oligonucleotides of 63 bases in length were annealed and repaired by Klenow fragment of DNA polymerase I in the presence of four $^{32}$P-dNTP according to Maniatis, T. et al. supra.

Northern blot analysis was performed as described by Maniatis, T. et al. supra, to verify the hybridization specificity of the designed oligonucleotide probe to antistasin mRNA and to determine the size of the antistasin mRNA. Upon hybridization, the oligonucleotide probe detected 750 base RNA as an apparently single sharp band. Since there was no detectable cross-hybridization with other RNA species, the size of antistasin mRNA was assigned as 750 bases.

From the isolated poly A+ RNA, a λgt22 expression-cDNA library was constructed according to Han, J. et al, Nucleic Acids Research 15, 6304 (1987). Two bacteriophage RNA polymerase promoters, SP6 and T7, were introduced into double-stranded cDNA and cloned into SalI and NotI sites of λgt22 in one orientation. About 2×10$^6$ primary independent cDNA clones were obtained. Screening was performed with an oligonucleotide probe according to Ullrich, A. et al., supra; or with an antibody probe as described by Young, R.A. et al., Science 222, 778 (1983). Fifty oligonucleotide positives and ten antibody positives were obtained from 5×10$^6$ recombinant clones. The oligonucleotide positive clone (λANS 0-13) with the largest insert (650 bp) was analysed for the nucleotide sequencing.

The nucleotide sequence was determined by direct λ sequencing or double-stranded sequencing after subcloning the cDNA insert in pUC18 according to Chen, E. et al. DNA 4 165 (1985). The sequence is presented in Table 7.

Antistasin mRNA has one long open reading frame positioned between about 23 bases of 5'-untranslated sequence and about 183 bases of 3'-untranslated sequence followed by the poly A site and poly A tail. Computer translation of the open reading frame (Table 7) showed a protein of 134 amino acids with a sequence which matched protein sequencing data. A leader peptide sequence of 17 hydrophobic amino acids was also found. Amino acid sequence determination on mature antistasin indicated that signal cleavage occurs after cysteine (residue #17). The mature antistasin does not contain the N-linked glycosylation site.

Recombinant antistasin produced from ANS 0-13 is serologically active. The mRNA was synthesized in vitro from λ ANS 0-13 DNA by T7 RNA polymerase according to Melton et al., Nucleic Acids Research 12, 7036 (1984). The antistasin mRNA was translated in vitro using a rabbit reticulocyte lysate, immunoprecipitated by rabbit antistasin antibody and analysed by SDS-polyacrylamide gel electrophoresis. In parallel, poly A+ RNA from leech salivary gland was also translated and immunoprecipitated as a positive control. The translation products from both the control and experiment were selectively immunoprecipitated by antibody as two indistinguishable 17,000 dalton bands.

TABLE 1

| Amino Acid Composition of the Antistasin, Stage 1 Purity[a] | | | |
|---|---|---|---|
| Amimo Acid | n moles | Ratio | # of Residues |
| Asx | 1.74 | 9.2 | 9 |
| Thr | 0.80 | 4.2 | 4 |
| Ser | 1.01 | 5.3 | 5 |
| Glx | 1.82 | 9.6 | 10 |
| Pro | ND[b] | | |
| Gly | 1.87 | 9.8 | 10 |
| Ala | 0.53 | 2.8 | 3 |
| Cys | 1.51 | 8.0 | 8 |
| Val | 0.46 | 2.4 | 2 |
| Met | 0.36 | 1.9 | 2 |
| Ile | 0.61 | 3.2 | 3 |
| Leu | 0.85 | 4.5 | 5 |
| Tyr | 0.34 | 1.8 | 2 |
| Phe | 0.48 | 2.5 | 3 |
| His | 0.19 | 1.0 | 1 |
| Lys | 1.44 | 7.6 | 8 |
| Arg | 1.40 | 7.4 | 7 |

[a]Average of two determinations, expressed as n mole per 28 μg of protein
[b]ND, not determined

| Amino Acid Composition of Antistasin, Stage 1 Purity, Second Analysis[a] | |
|---|---|
| Amino Acid | # of residues Per 17,000 Mr |
| Asx | 11.1 |
| Thr | 8.9 |
| Ser | 8.7 |
| Glx | 13.5 |
| Pro | 12.2 |
| Gly | 17.4 |
| Ala | 6.5 |
| Cys | ND |
| Val | 4.3 |
| Met | 2.2 |
| Ile | 4.3 |
| Leu | 6.3 |
| Tyr | 29 |
| Phe | 4.5 |
| His | 3.3 |
| Lys | 3.9 |
| Arg | 12.6 |

[a]464 ng of protein was analyzed
[b]ND, not determined

TABLE 2

| % Inhibition of Lung Tumor Colonies by Antistasin, Stage 1 Purity | | | |
|---|---|---|---|
| Sample | Amount Injected (μg/mouse) | Number Of Mice | % Inhibition[a] |
| Experiment 1 | | | |
| SGE[b] | 1000 | 5 | 100 |
| Antistasin | 15 | 4 | 85 |
| Experiment 2 | | | |
| SGE | 1000 | 4 | 89 |
| Antistasin | 62 | 4 | 100 |
| Experiment 3 | | | |
| SGE | 1000 | 7 | 97 |
| Antistasin | 73 | 7 | 93 |

[a]% inhibition is calculated as follows: median number lung tumors of control animals minus median number of lung tumors of treated animals divided by the median number of lung tumors from control animals times 100. The median number of lung tumors of control animals ranged from 20–60 tumors per animal. That of treated animals ranged from 0–5 tumors per animal.
[b]SGE = crude Leech Salivary Gland Extract

TABLE 3

| The Effect of Antistasin on the Prothrombin and Activated Partial Thromboplastin Times | | |
|---|---|---|
| Addition | Clotting Time (sec)[a] | Difference[b] |
| Buffer | 95.6, 12.8 | — — |
| Antistasin[c] | 152.1, 82.8 | 56.5, 70.0 |

[a]Each value is the average of two determinations. Clotting times were obtained with normal human pooled plasma. The first clotting time is the activated partial thromboplastin time and the second time is the prothrombin time.
[b]Difference is protein minus buffer control. The first value is that calculated for the activated partial thromboplastin time and the second value is that for the prothrombin time.
[c]Two μg of protein, Stage 1 purity, were added to the test plasma.

TABLE 4

| The Effect of Antistasin, Stage 1 on the Clotting Time of Thrombin and Factor Xa | | | |
|---|---|---|---|
| Protein (μg) | Clotting Time (sec) | Protein (μg) | Clotting Time (sec) |
| Thrombin | | Factor Xa | |
| 0 | 33.9, 22.2[a] | 0 | 25.9 |
| 2.42 | 31.4, 20.6[a] | 1.21 | 275.9 |
| | | 2.42 | 1369.5 |

[a]The first clotting time was obtained using 1 mg/ml fibrinogen as substrate and the second was obtained using normal human plasma as substrate. Factor Xa clotting times were obtained using human factor X deficient plasma. Clotting times are an average of two determinations. Thrombin and factor Xa present in the assay mixtures were 0.30 and 0.10 units, respectively.

TABLE 5

| Amino Acid Composition of Antistasin, Stage 2 purity, Mr - 17,000 | |
|---|---|
| Amino Acid | Residues per Mr - 17,000 |
| Asp | 11 |
| Thr | 5 |
| Ser | 8 |
| Glu | 14 |
| Pro | 10 |
| Gly | 13 |
| Ala | 4 |
| Val | 2 |
| Ile | 5 |
| Leu | 7 |
| Tyr | 2 |
| Phe | 3 |
| Lys | 11 |
| His | 2 |
| Arg | 15 |
| Met | 3 |
| Cys | 20 |

TABLE 6
ANTISTASIN: AMINO ACID SEQUENCE, INCLUDING KNOWN VARIANTS

```
                                      ARG                       10
PYROGLU—GLU—PRO—PHE—GLY—PRO—GLY—CYS—GLU—GLU—ALA—GLY—CYS—PRO—GLU—GLY—SER—

20                                          GLU  31              VAL
ALA—CYS—ASN—ILE—ILE—THR—ASP—ARG—CYS—THR—CYS—SER—GLY—VAL—ARG—CYS—ARG—MET—

40                                       50
HIS—CYS—PRO—HIS—GLY—PHE—GLN—ARG—SER—ARG—TYR—GLY—CYS—GLU—PHE—CYS—LYS—CYS—

ILE                      60                                       70
ARG—LEU—GLU—PRO—MET—LYS—ALA—THR—CYS—ASP—ILE—SER—GLU—CYS—PRO—GLU—GLY—MET—

80
MET—CYS—SER—ARG—LEU—THR—ASN—LYS—CYS—ASP—CYS—LYS—ILE—ASP—ILE—ASN—CYS—ARG—

90                                      100
LYS—THR—CYS—PRO—ASN—GLY—LEU—LYS—ARG—ASP—LYS—LEU—GLY—CYS—GLU—TYR—CYS—GLU—

110                                   119
CYS—ARG—PRO—LYS—ARG—LYS—LEU—ILE—PRO—ARG—LEU—SER—COOH
```

TABLE 7
NUCLEOTIDE SEQUENCE OF ANS 0-3

| | | |
|---|---|---|
| 1 | TTGACTAATTAGAATAATTTATGATGATTAAGTTGGCTATTTTATTGCTGTTCACTGTTGCCATAGTC<br>METMETILE LYS LEUALAILE LEULEULEUPHETHRVALALALAILE VAL | 68 |
| 69 | CGTTGTCAAGGACCATTTGGACCCGGGTGTGAAGAGGCAGGATGTCCAGAAGGTTCCGCGTGCAACATT<br>ARGCYSGLNGLY PROPHEGLY PROGLY CYS GLUGLU ALA GLY CYS PROGLUGLY SER ALA CYS ASN ILE | 137 |
| 138 | ATTACAGACAGATGCACTTGTTCTGGGGTCAGATGTCGTATGCACTGTCCGCATGGATTTCAGAGGAGC<br>ILE THRASP ARGCYS THRCYS SERGLY VALARGCYS ARGMETHIS CYSPROHIS GLY PHEGLNARGSER | 206 |
| 207 | AGATACGGGTGTGAATTCTGCAAATGCATATTGGAGCCAATGAAAGCTACATGTGACATAAGCGAATGC<br>ARGTYRGLY CYSGLUPHECYS LYS CYS ILE LEUGLU PROMETLYS ALATHR CYS ASP ILE SER GLU CYS | 275 |
| 276 | CCAGAAGGTATGATGTGTAGCAGACTGACCAATAAGTGTGATTGCAAGATAGACATCAACTGCAGAAAA<br>PROGLUGLYMETMETCYS SER ARGLEUTHRASNLYS CYS ASP CYS LYS ILE ASP ILE ASN CYS ARGLYS | 344 |
| 345 | ACCTGTCCAAACGGCCTCAAACGTGATAAACTTGGATGCGAATATTGTGAATGTAGGCCCAAGAGGAAG<br>THRCYSPROASNGLYLEULYS ARGASP LYS LEUGLY CYS GLUTYRCYSGLUCYS ARGPROLYS ARGLYS | 413 |
| 414 | CTTATCCCACGCTTATCATAATATATGTATATATATATATATATATATATATATATTATATACCATAATATA<br>LEUILE PROARGLEUSER | 483 |
| 484 | TATATACCATATATATATATACCATATATATATATACCATATGTGTATATATATATATATATATTATCC | 552 |
| 553 | CTATTATTGATTAAAGTTGATAAATTAATAATGATAAGGAATTTGAAATAAAAAATTGATTTTGACAAA<br>AAAAAAAAAAAAAAA    636 | 621 |

What is claimed is:

1. A biochemically pure protein antistasin having a molecular weight of about 17,000 and an iso-electric point of 9.5, and a capacity to inhibit or delay blood coagulation by selective inhibition of coagulation factor Xa, as indicated by inhibition of coagulation factor Xa and non-inhibition of thrombin-induced coagulation, said protein having the amino acid sequence of antistasin from salivary glands of the leech *Haementeria officinalis*.

2. The purified protein of claim 1 wherein said protein possesses antimetastatic properties.

3. The protein of claim 1, said protein having the following amino acid composition:

| Amino Acid | n moles per 28 micro grams of protein |
|---|---|
| Asx | 1.74 |
| Thr | 0.80 |
| Ser | 1.01 |
| Glx | 1.82 |
| Gly | 1.87 |
| Ala | 0.53 |
| Cys | 1.51 |
| Val | 0.46 |
| Met | 0.36 |
| Ile | 0.61 |
| Leu | 0.85 |
| Tyr | 0.34 |
| Phe | 0.48 |
| His | 0.19 |
| Lys | 1.44 |
| Arg | 1.40 |

4. A process for the production of a protein derived from the salivary gland of the leech *Haementeria officinalis*, said process comprising the steps of:
   a) dissecting and removing the salivary gland tissue of said leech;
   b) homogenizing and solubilizing said salivary gland tissue in an aqueous solution comprising a buffered salt having a fixed pH of 7.8 to produce a homogenate; and c) centrifuging said homogenate to produce supernatant protein suspension fractions, and by assaying said supernatant fractions and selecting a product fraction characterized by its inhibition of coagulation factor Xa, said supernatant fraction being separated at a force of at least 100,000 g for a period of at least 1 hour, and said 100,000 g supernatant fraction is further treated by the steps of d) placing said supernatant fraction in contact with a column of heparin agarose equilibrated with Tris buffer, pH 8.7;

e) separating fractions containing proteins which are not adsorbed on said column from fractions containing proteins which are adsorbed on said column; and f) selecting from said adsorbed fractions, a protein having anticoagulant properties.

5. The process of claim 4 further including the steps of:

g) eluting a first portion of said adsorbed fractions using a buffered salt solution until spectrophotometric absorbance at 280 nM is no longer detected;

h) eluting a second portion of said adsorbed fractions using a gradient elution liquid comprising 20 mM Tris buffer and 1M NaCl in Tris buffer; and testing the eluted fractions to identify an eluate fraction possessing anticoagulant activity.

6. A process, as recited in claim 5, further including:

i) concentrating said eluate fractions having anticoagulant activity by centrifugation through ultrafilters having molecular weight exclusion limits of about 12,000 j) de-salting said concentrated eluate fraction;

k) adsorbing said de-salted concentrated eluate fraction on a Mono-Q anion exchange column; and l) eluting said adsorbed fraction with NaCl step gradient in the range of 0.10-0.30M in Tris buffer solution to yield antistasin.

7. The product of claim 4 wherein said protein is characterized by in vitro inhibition activity for coagulation factor Xa.

8. The product of claim 4 wherein said protein antistasin is characterized by antimetastatic properties.

9. A method of treating a mammal for the prevention of metastasis comprising administering to said mammal in a therapeutically effective dose, a biochemically pure protein, as recited in claim 1.

10. A method for treating a mammal to prolong blood clotting time comprising administering to said mammal an effective dose of a biochemically pure protein, as recited in claim 1.

11. The product of claim 5 wherein said protein is characterized by in vitro inhibition activity for coagulation factor Xa.

12. The product of claim 5 wherein said protein is characterized by antimetastatic properties.

13. The product of claim 6 wherein said protein is characterized by in vitro inhibition activity for coagulation factor Xa.

14. The product of claim 6 wherein said protein is characterized by antimetastatic properties.

* * * * *

UNITED STATES PATENT AND TRADEMARK OFFICE
CERTIFICATE OF CORRECTION

PATENT NO.  : 5,194,589

DATED       : March 16, 1993

INVENTOR(S) : John A. Bott

It is certified that error appears in the above-identified patent and that said Letters Patent is hereby corrected as shown below:

On the title page, in item [75], "John A. Bott, Grosse Pointe Shores, Mich." should be deleted, and insert therefor the following:

--Gabriel J. Gasic; Tatiana B. Gasic, both of Gulph Mills, Pa.; George P. Tuszynski, Williamstown, N.J.; Gregory P. Gasic, San Diego, Calif.--.

Signed and Sealed this

Eleventh Day of May, 1993

Attest:

MICHAEL K. KIRK

Attesting Officer

Acting Commissioner of Patents and Trademarks